United States Patent [19]

Tanabe et al.

[11] 4,009,077

[45] Feb. 22, 1977

[54] PROCESS FOR THE PREPARATION OF PHENOPICOLINIC ACID

[75] Inventors: Osamu Tanabe; Akira Obayashi, both of Uji; Teruya Nakamura, Muko; Osamu Suzuka, Kyoto; Masao Murayama, Kyoto; Shingo Matsumura, Kyoto, all of Japan

[73] Assignee: Nippon Shinyaku Co., Ltd., Japan

[22] Filed: Aug. 22, 1975

[21] Appl. No.: 607,039

Related U.S. Application Data

[63] Continuation-in-part of Ser. No. 582,766, June 2, 1975, abandoned.

[52] U.S. Cl. .............................. 195/81; 260/297 R; 424/263

[51] Int. Cl.$^2$ ......................................... C12D 13/02
[58] Field of Search .................................... 195/81

[56] References Cited

UNITED STATES PATENTS 3,847,742  11/1974  Higgens et al. ..................... 195/81

*Primary Examiner*—Alvin E. Tanenholtz

[57] ABSTRACT

Phenopicolinic acid is produced by culturing a strain of Paecilomyces. The compound, which may be alternatively named as 5-(4-hydroxybenzyl)-2-pyridinecarboxylic acid, is a hypotensive agent.

2 Claims, No Drawings

PROCESS FOR THE PREPARATION OF PHENOPICOLINIC ACID

CROSS REFERENCE

This is a continuation-in-part of Ser. No. 582,766 filed June 2, 1975, now abandoned.

DETAILED DESCRIPTION

This invention relates to the preparation of a novel biologically active substance, phenopicolinic acid. Phenopicolinic acid is 5-(4-hydroxybenzyl)2-pyridine carboxylic and can be diagramatically depicted the following structure:

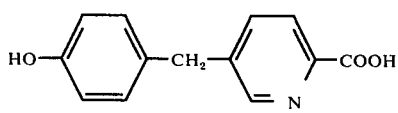

This invention embraces the microbiological preparation of phenopicolinic acid and its, salts, whether in purified solid, either crystalline or amorphous, forms, as diluent solutions, crude concentrates, or crude solids, which can be used in achieving a hypotensive; i.e., antihypertensive, effect in animals including humans.

While engaged in research yielding biologically active substances of microbial origin, a novel, biologically active substance was discovered which inhibited enzymatic activity of dopamine beta-hydroxylase and thus demonstrated potent hypotensive effect. This material, which we have named "phenopicolinic acid", is accumulated in the culture broths of microorganisms belonging to the genus Paecilomyces. The typical strain producing phenopicolinic acid was isolated from a soil by us and named Paecilomyces sp. AF 2562. (This strain has been deposited with the Fermentation Research Institute, Agency of Industrial Science and Technology, Ministry of International Trade and Industry, Japan, under the deposit number 2355, and with the American Type Culture Collection, under deposit number ATCC 20463.) The cultural characteristics, morphology and physiological properties of this microorganism, as well as the methods for production and recovering the substance from the culture broth, can be summarized as follows:

The Paecilomyces sp. AF 2562 has the following microbiological properties.

I. Cultural Characteristics on Various Media (27° C, 2 weeks) and Morphology

1. Malt extract agar:
   Good Growth; white to light brown cotton-like mycelium; reverse light brown; color in medium light brown.
2. Potato glucose agar:
   Good growth; white to light brown cotton-like mycelium; reverse light brown; color in medium yellow.
3. Czapek's agar:
   Good growth; central portion of colony white to light orange cotton-like and peripheral portion spreading thinly; reverse brown; color in medium light yellow.
4. Sabouraud's agar:
   Good growth; white to slightly brown cotton-like mycelium; reverse brown wrinkled; color in medium yellowish brown.
5. Oatmeal agar:
   Rather poor growth; white mycelia expanding on agar surface relatively sparsely; reverse light yellow; color in medium light yellow.
6. YpSs agar:
   Good growth; white to light brown cotton-like mycelium; reverse brown wrinkled; color in medium yellowish brown.

In each of the foregoing media, formation of spores is good. Aerial mycelia develop well and irregular branches are observed. Conidiophores arise from aerial mycelia or vegetative mycelia. One to five long (10 – 20 $\mu$) phialides, which taper gradually towards the apex, are frequently verticillated.

Phialospores are extruded from the apex of phialides and lie broadside on, and are irregularly shifted to one another, forming long chains, sometimes gathering to form globes. They are cylindrical with rounded ends, 3 to 5 $\mu$ long and 1.5 to 2 $\mu$ wide, and non-septate.

II. Physiological Properties:

1. Growth conditions:
   pH: 2 to 12 with the optimum pH being 5 to 6.
   Temperature: 10° to 35° C. with optimum temperatures being within a range of 20° to 27° C.
2. Utilization of Carbon Source:
   3% of a carbon source indicated below was added to a liquid medium containing 0.5% of polypeptone and 0.1% of yeast extract. The culture was shaken at 27° C. to yield the following growth results growth state of cells:

Glucose: ++ (good growth)
Galactose: ++ (good growth)
Mannose: ++ (good growth)
Fructose: ++ (good growth)
Sucrose: ++ (good growth)
Maltose: ++ (good growth)
Lactose: ++ (good growth)
Dextrin: ++ (good growth)
Soluble starch: ++ (good growth)
Glycerol: ++ (good growth)
Sorbitol: + (moderate growth)
Cellulose: + (moderate growth)
Inulin: + (moderate growth)
Soybean oil: ++ (good growth)
Tartaric acid: ± (scanty growth)
Citric acid: ± (scanty growth)
Succinic acid: ± (scanty growth
Fumaric acid: : ± (scanty growth)

When the present strain is examined on the above observations by the criteria of H. L. Barnett, *Illustrated Genera of Imperfect Fungi*, 3rd edition, 1972, and G. L. Barron, *The Genera of Hyphomycetes from Soil*, it is apparent that the present strain belongs to the genus Paecilomyces.

The particular strain which has been deposited, Paecilomyces sp. AF 2562, is merely typical of the microorganism which can be used in this invention and any strain belonging to the genus Paecilomyces which produces phenopicolinic acid can be used in this invention. Artificial mutants formed by irradiating these strains with ultraviolet rays or treating them with a chemical mutagen such as nitrosoguanidine, as well naturally occurring mutants of these strains, were found to have phenopicolinic acid-producing activity, and these mutants can also be used in this invention.

For the production of phenopicolinic acid according to the present invention, a phenopicolinic acid-producing strain of Paecilomyces is cultured using the known methods for culturing microorganisms. Either a liquid culture method or a solid culture method can be adopted in this invention. In the case of the liquid culture method, the culturing can be stationary or carried out under shaking or aeration. In general, a shaking culture method or aeration agitation culture method in a liquid medium is preferred in this invention.

Any of the many media customarily used for culturing microorganisms can be employed in this invention. More specifically, as the carbon source, there can be employed, for example, saccharides such as glucose, galactose, fructose, mannose, lactose, melibiose, dextrin, starch, glycerin and sorbitol, and vegetable and animal oils and fats such as soybean oil and lard. As the nitrogen source, there can be employed, for example, yeast extract, meat extract, soybean powder, cotton seed powder, corn steep liquor, amino acids such as glutamic acid, aspartic acid, tyrosine and phenylalanine, salts of these amino acids, urea, ammonium salts and nitrates. Further, inorganic salts of phosphoric acid, magnesium, calcium, sodium, potassium, iron, manganese and the like, and minute amounts of nutrients such as vitamins can optionally be added. Still in addition, cells of microorganisms such as yeast and bodies of plants and animals, or extracts thereof can optionally be added. It is possible to increase the amount formed of the intended product by adding to a culture medium cinnamic acid, p-hydroxycinnamic acid, a halogenated cinnamic acid, cinnamyl alcohol, or a simple derivative thereof, e.g., a salt or ester, of course, these culturing ingredients or additives may be added in the course of the culturing rather than the outset.

Culturing conditions such as the pH of the culture medium, the culturing temperature and the culturing period can be adjusted, optionally within the disclosed ranges to provide the product. The culturing is preferably carried out at 20° to 30° C. for 2 to 10 days in pH of 3 to 7.

When the culturing is carried out in the above-mentioned manner, phenopicolinic acid is formed and accumulated in the culture broth. This substance can be collected from either the filtrate of the culture filtrate or mycelia. In case of a liquid culture, the intended substance is present mainly in the liquid portion of the culture broth. Accordingly, after completion of the culturing, the liquid portion is preferably separated from the culture broth, as by filtration using a filter-aid such as Celite. Recovery of the intended substance from the filtrate is accomplished by utilizing customary means for separation and purification of organic substances, such as adsorption using an ion exchange resin, organic solvent extraction and/or adsorption chromatography. More specifically, the filtrate separated from the culture broth or liquid containing the intended substance is passed through a column packed with a strong acidic cation exchange resin such as Dowex 50W (H type) and Amberlite IRC-120 (H type) or a basic anion exchange resin such as DEAE Cellulose (OH type) and Amberlite IR-45 (OH type), to thereby make the intended substance adsorbed on such ion exchange resin, and the intended substance is eluted with a solution of an acid, alkali or salt. The pH of the filtrate separated from the culture broth or aqueous solution containing the intended substance is rendered acidic and extracted with an organic solvent such as ethyl acetate and butanol, whereby the intended substance is transferred into the organic solvent layer. When this organic solvent layer is separated and concentrated under reduced pressure, the crude product is obtained. Purification of the product can be accomplished by adsorbing it on a column packed with an adsorbant such as alumina or silica gel and developing it with benzene, chloroform, ethyl acetate, methanol or diluent aqueous ammonia or a suitable mixture thereof. When the eluant containing the intended substance is concentrated under a reduced pressure and the concentrate is allowed to stand still in a cool place, the intended substance is recovered in the form of light yellow crude crystals.

Recrystallization of this crude crystals from a suitable solvent such as methanol yield colorless crystals of the intended substance, phenopicolinic acid. Purified phenopicolinic acid is a colorless crystalline material having a melting point of 222° to 226° C.

On analysis, the substance contains carbon, hydrogen, nitrogen and oxygen, the results of elementary analysis being as follows:

$C = 68.06\%$, $H = 5.13\%$, $N = 6.20\%$

The mass spectrum of the methylated product shows a molecular weight is 229. Accordingly, the substance has a molecular formula $C_{13}H_{11}O_3N$. The ultraviolet absorption spectrum of the substance shows a maximum absorption at 271 m$\mu$ ($\epsilon$, 10.1 $\times$ 10$^3$) in 1N hydrochloric acid. No maximum is observed, but shoulders are present, at about 277 m$\mu$ and 300 m$\mu$ in 1N sodium hydroxide. In the infrared absorption spectrum (KBr) absorptions are observed at 3030, 1655, 1590, 1515, 1440, 1385, 1305, 1280, 1245, 1230, 1220, 1175, 1120, 825 and 800 cm$^{-1}$.

The substance has no optical activity and is soluble in methanol and water, sparingly soluble in acetone, ethyl acetate and chloroform, and insoluble in benzene and n-hexane. It decolorizes potassium permanganate and is positive to ninhydrin reaction, Millon's reaction and ferrous sulfate reaction (1% acetic acid solution). An aqueous solution of the substance is colorless and acidic.

The substance inhibits dopamine beta-hydroxylase. When this inhibition is measured according to the method of Nagatsu et al [Chemical and Pharmaceutical Bulletin, 17 2377 (1969)], it is found that the 50% inhibition concentration is 8.9 $\times$ 10$^{-9}$ g per ml (3.9 $\times$ 10$^{-8}$ M). The inhibition is uncompetitive to tyramine but competitive to ascorbic acid, and the inhibition coefficient is 5 $\times$ 10$^{-9}$ M. The potent hypotensive effect of phenopicolinic acid can be conveniently observed in recognized laboratory models. Thus in the spontaneously hypertensive rats, 50 mg/kg of phenopicolinic acid administered orally produced a decrease in blood pressure of 21, 16 and 23% in 1, 3 and 5 hours, respectively, after administration. The acute toxicity (LD$_{50}$) of the substance is 354 mg/kg when it is administered to mice of the dd-system by intraperitoneal injection.

The pharmaceutical compositions of the present invention contain a major or minor amount, e.g. 99.5% to 0.1%, preferably 95% to 0.5%, of phenopicolinic acid or a salt thereof in combination with a pharmaceutically acceptable nontoxic, inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of phenopicolinic acid corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired antihypertensive effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the hypertensive condition, generally the dosage will be from about 15 to about 100, preferably 20 to 45, mg/kg of body weight per day when given orally, and from about 3 to about 20, preferably from 7 to 15, mg/kg of body weight per day when given parenterally. In some instances a sufficient antihypertensive effect can be obtained at a lower dose while in others, a larger dose will be required.

Typical daily doses for hypertensive patient of about 70 kg body weight are thus from about 100 to 800 mg, preferably 150 to 30 mg, and typical parenteral doses are from 20 to 150 mg, preferably 50 to 100 mg.

Oral administration can be effected utilizing solid and liquid dosage unit forms such as powders, tablets, dragees, capsules, granulates, suspensions, solutions and the like.

Powders are prepared by communicating the compound to a suitable fine size and mixing with a similarly comminuted pharmaceutical carrier such as an edible carbohydrate as for example starch, lactose, sucrose, glucose or mannitol. Sweetening flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl, cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. Phenopicolinic acid and its salts can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of phenopicolinic acid. Syrups can be prepared by dissolving the compound or a salt thereof in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of phenopicolinic acid is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

As indicated, the present invention also pertains to the physiologically acceptable salts of phenopicolinic acid with alkali metals, alkaline earth metals, ammonia and organic amines as, for example, the sodium salt, the potassium salt, the calcium salt, and the salts with amines such as ethylamine, triethylamine, ethanolamine, diethylaminoethanol, ethylenediamine, piperidine, morpholine, 2-piperidinoethanol, benzylamine, procaine and the like.

The following examples will serve to further typify the nature of this invention without being a limitation on the scope thereof.

EXAMPLE 1

Paecilomyces sp. AF 2562 was cultured for 3 weeks on Czapek's agar slant. Each of 50 of 500-ml capacity shaking flasks was charged with 100 ml of a culture medium (pH × 6.6) containing 3% of glucose, 0.5% of polypeptone and 0.1% of yeast extract and sterilized at 120° C. for 15 minutes. Mycelia cut from the slant culture medium were inoculated into one of the above flasks, and shaking culture was carried out at 30° C. for 2 days. The remaining 49 flasks were each inoculated aseptically with 1 ml of the resulting culture broth and were shake cultured at 30° C. for 7 days. The culture broth in the flasks were combined and filtered to remove mycelia and obtain 4.4 lit of a filtrate. The filtrate was applied to a 1-liter column of Dowex 50W (H type). The ion exchange resin was washed with water sufficiently and then product was eluted with 1N aqueous ammonia. The resulting fraction (1.7 lit) was concentrated under reduced pressure, and the concentrate was dissolved in 100 ml of water and the pH adjusted to 2.0. The aqueous solution was extracted 3 times with equal amounts of ethyl acetate, and the ethyl acetate extracts were combined and concentrated under reduced pressure. The concentrate was dissolved in a small amount of methanol and coated on 2 g of silica gel (Mallinckrodt) by removing methanol. The above silica gel was added to 300 ml of a silica gel column filled with chloroform, and 1.5 liter of chloroform was passed through the column to effect washing. Development was conducted with 19 : 1 chloroform-methanol. The active fractions were combined and concentrated. The concentrate was dissolved in a small amount of methanol and applied to 200 ml of a neutral alumina column filled with methanol. Five hundred milliliters of methanol were passed through the column to effect washing and development was conducted with 4 : 1 methanol-4N aqueous ammonia. The active fractions were collected and concentrated under reduced pressure. The concentrate was dissolved in 30 ml of water and the pH was adjusted to 2.0. The aqueous solution was extracted 3 times with equal amounts of ethyl acetate, and the ethyl acetate extracts were combined and concentrated under reduced pressure to yield light yellowish white crystals. The crude crystals were recrystallized from methanol to yield about 4 mg of phenopicolinic acid in the form of colorless crystals.

EXAMPLE 2

Each of 10 to 30-liter capacity stainless steel fermentation tanks was charged with 20 liters of a culture medium containing 0.5% of polypeptone, 0.1% of yeast extract and 0.05% of a defoaming agent KM 70 (Shinetsu Kagaku), and the medium was sterilized at 120° C. for 30 minutes. After cooling, each fermentation tank was aseptically inoculated with two flasks of a culture broth obtained by shaking-culturing in the same manner as described in Example 1. The culturing was carried out under agitation of 250 r.p.m. by introducing air in an amount of 25% by volume based on the culture medium per minute. A defoaming agent was added as needed. The culturing was continued for 3 days, and the culture broth was filtrated to remove mycelia. Then, 160 liters of the filtrate were applied to a 10-liter column of Dowex 50W (H type), washed sufficiently with 40 liters of water, and the intended substance was eluted with 1N aqueous ammonia. Sixty liters of the active fraction were collected, and the pH was adjusted to 2.0 with hydrochloric acid and the liquid was extracted 3 times with a half volume of ethyl acetate. The ethyl acetate layers were combined and concentrated under reduced pressure. The concentrate was dissolved in a small amount of methanol and applied to a 1-liter column of alumina filled with methanol. The column was washed with 5 liters of 9 : 1 methanol-4N aqueous ammonia and the intended substance was developed with 4 : 1 methanol-4N aqueous ammonia.

The active fraction was concentrated and dissolved in 300 ml of water. The pH of the solution was adjusted to 9.5 and the solution was extracted with an equal amount of ethyl acetate. The ethyl acetate layer was discarded and the pH of the water layer was adjusted to 2.0 and the water layer was extracted 3 times with small amounts of ethyl acetate. The ethyl acetate layers were combined and concentrated under reduced pressure. The concentrate was dissolved in a small amount of methanol and coated on 20 g of silica gel by removing methanol. The above silica gel was added a 1 liter silica gel column filled with chloroform, and 3 liters of chloroform were passed therethrough. Development was conducted with 19 : 1 chloroform-methanol. The active fractions were collected and concentrated under pressure to yield light yellowish white crystals. The crude crystals were recrystallized from methanol to yield about 200 mg of phenopicolinic acid in the form of colorless crystals.

What is claimed is:
1. Process for preparation of phenopicolinic acid of the formula:

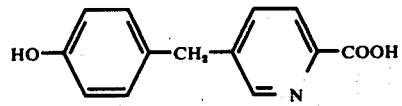

which comprises culturing a phenopicolinic acid producing strain of the genus Paecilomyces, under aerobic conditions in a medium containing one or more assimilable sources of carbon and one or more assimilable sources of nitrogen, and isolating the phenopicolinic acid thus formed from the culture broth.

2. The process according to claim 1 wherein the strain is Paecilomyces sp. AF 2562 (ATCC 20463).

* * * * *